United States Patent
Garneau

[11] Patent Number: 5,704,072
[45] Date of Patent: Jan. 6, 1998

[54] OCCIPITAL RETENTION STRAP FOR CYCLIST HEADGEAR

[75] Inventor: Louis Garneau, St-Augustin-de-Desmaures, Canada

[73] Assignee: 9001-6262 Québec Inc., St-Augustin-de-Desmaures, Canada

[21] Appl. No.: 678,542

[22] Filed: Jul. 5, 1996

[51] Int. Cl.$^6$ .................................................. A42B 3/00
[52] U.S. Cl. ................................. 2/421; 2/909; 24/442
[58] Field of Search ........................... 2/410, 411, 421, 2/422, 417, 418, 425, 908, 909, 910, 911, 918, 920; 24/442, 306, 265 WS, 625

[56] References Cited

U.S. PATENT DOCUMENTS

| | | | |
|---|---|---|---|
| 4,805,239 | 2/1989 | Ciago | 2/911 |
| 4,898,162 | 2/1990 | Worthrich | 2/909 |
| 5,044,019 | 9/1991 | Shewchenko et al. | 2/421 |
| 5,381,560 | 1/1995 | Halstead | 2/421 |
| 5,551,094 | 9/1996 | Navone | 2/421 |
| 5,581,819 | 12/1996 | Garneau | 2/421 |
| 5,617,589 | 4/1997 | Lacore et al. | 2/909 |
| 5,619,754 | 4/1997 | Thurwanger et al. | 2/418 |

FOREIGN PATENT DOCUMENTS

| | | | |
|---|---|---|---|
| 95/01739 | 1/1995 | WIPO | 2/421 |

*Primary Examiner*—Michael A. Neas
*Attorney, Agent, or Firm*—François Martineau

[57] ABSTRACT

The present invention is a stabilizing strap for a cyclist helmet which comprises two flexible elongated strap members which are adjustably and releasably attached at their first end to the interior surface of the helmet rim portion, at the rear end of the helmet, by means of hook and loop fasteners. The strap members are adjustably and releasably attached at their second end to one another also by means of hook and loop fasteners. The curved strap is destined to bear on the occipital bone of the head, to prevent the helmet from accidentally tilting frontwardly, especially as a result of an impact. The flexibility and the several adjustments of the stabilizing strap allow it to fit heads of different sizes and shapes.

11 Claims, 3 Drawing Sheets

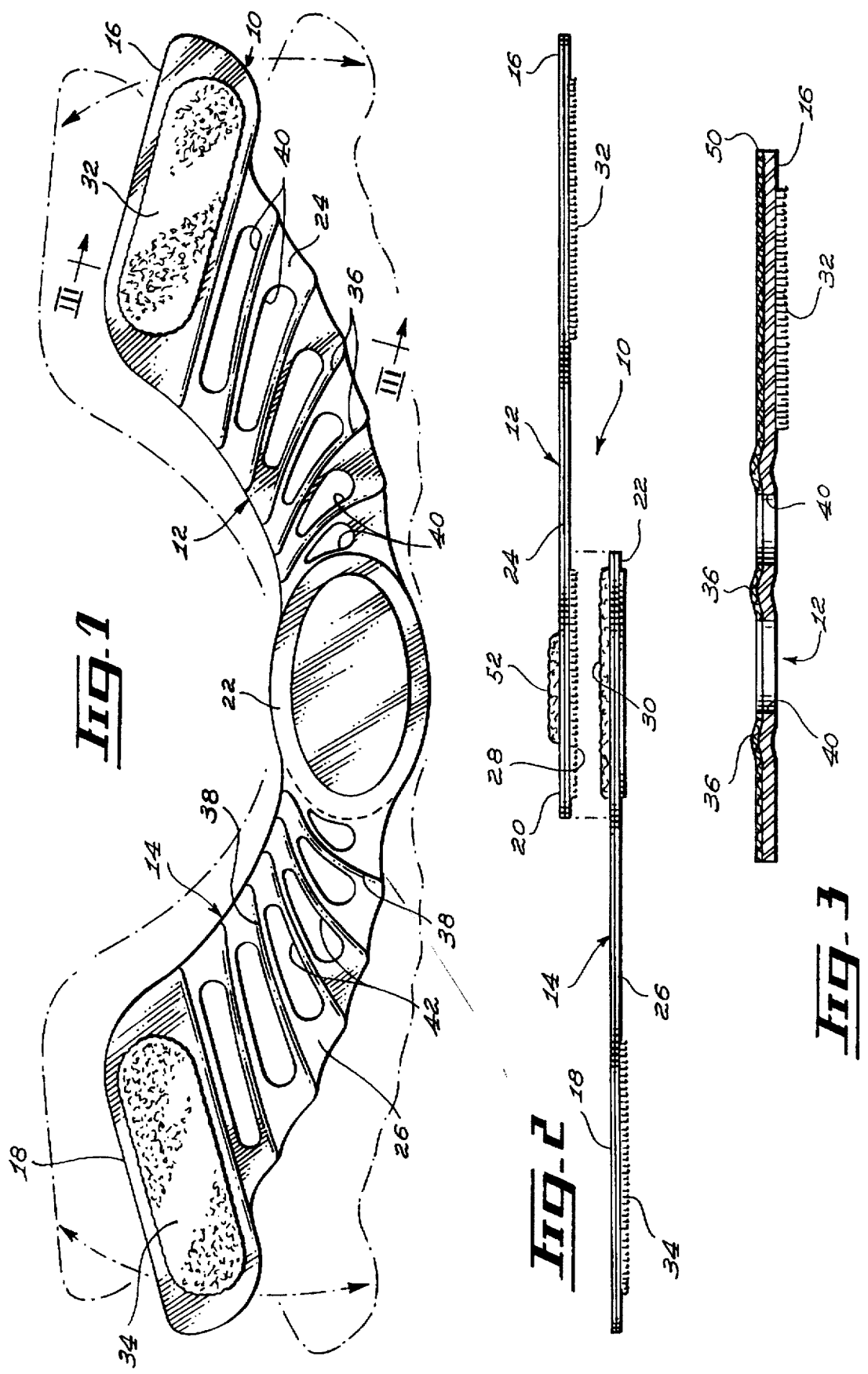

OCCIPITAL RETENTION STRAP FOR CYCLIST HEADGEAR

FIELD OF THE INVENTION

The present invention relates to safety helmets for cyclists, and more particularly to a stabilizing strap for a safety helmet.

BACKGROUND OF THE INVENTION

U.S. Pat. No. 5,351,342 issued in 1994 to the present applicant shows a conventional prior art safety helmet. This helmet is substantially domed-shaped and defines a lower peripheral rim portion. Fastening straps are adapted to be attached under the chin of the helmet wearer, to retain it more securely on the wearer's head. When the helmet is correctly worn, the fastening straps form a Y-shape on each side of the wearer's head, with one strap being positioned in front of the ear and one strap being positioned behind the ear, these two straps joining under the ear to extend under the chin and be attached to the other strap.

These fastening straps assist in maintaining the helmet securely attached to the wearer's head. Indeed, not only do they prevent the helmet from vertically moving off the wearer's head, but also they help prevent the helmet from pivoting off the front or the rear of the wearer's head.

The main problem with such a helmet is that although the helmet may not pivotally fall off the wearer's head, it is still allowed a considerable pivotal play towards the front of the wearer's head. Because of the position of one of the straps holding the front of the helmet and extending downwardly under the chin, an important backward pivotal movement is prevented. However, the position of the rear strap, which also extends under the chin, will allow a relatively important pivotal play of the helmet, which may result in exposing the back of the wearer's head dangerously during a multiple-impact fall.

OBJECTS OF THE INVENTION

It is an object of this invention to provide a stabilizing strap for a helmet that is adapted to securely bear on the wearer's head to prevent an accidental frontward tilting of the helmet.

It is another important object of the invention that the stabilizing strap be flexible and adjustable to fit heads of different sizes and shapes.

It is yet another object of the invention that the stabilizing strap be easily adjustable.

SUMMARY OF THE INVENTION

In accordance with the teachings of the invention, there is disclosed a flexible stabilizing strap for use on a cyclist helmet of a type having a shell with a rear end and a lower peripheral rim portion, said stabilizing strap comprising a first and a second separate elongated flexible curved strap members, each strap member comprising: a) a first end portion having first attachment means for releasable and adjustable attachment to the helmet rim portion proximate the shell rear end; b) a second end portion having second attachment means for adjustable and releasable attachment to the second end portion of the other strap member, said second attachment means of said first and second strap members being complementary to one another; and c) an intermediate ribbed portion, having several widthwise ribs conferring a greater flexibility to said strap member; said second end portions of said first and second strap members destined to be positioned spacedly under the rim portion at the helmet rear end; wherein the combined said second end portions attached to one another by said second attachment means constitute a means for relative movement of said first and second strap members relative to one another, both pivotally about an axis transverse to said attached second end portions, and arcuately along the flexible body of said intermediate portions of said first and second strap members.

Preferably, each strap member further comprises several substantially ovoidal apertures which are positioned at said ribbed portion and extending generally parallel to said ribs, for conferring a greater flexibility to said strap member. Said ribs and said apertures could then be positioned in an alternating fashion along said ribbed portion. Said first and second attachment means could be hook and loop fasteners, said second end portion of second strap member overlapping said first strap member when attached to one another.

The invention also relates to a protective helmet for cyclist comprising a stabilizing strap and defining a shell having a rear end and a lower peripheral rim portion on which is releasably and adjustably attached said stabilizing strap near said shell rear end, said stabilizing strap comprising a first and a second elongated flexible curved strap members, each strap member comprising: a) a first end portion having first attachment means adjustably and releasably attached to the helmet rim portion; b) a second end portion having attachment means adjustably and releasably attached to the second end portion of the other strap member, said second attachment means of said first and second strap members being complementary to one another; and c) an intermediate ribbed portion, having several widthwise ribs conferring a greater flexibility to said strap member; wherein said stabilizing strap defines an operative position when said first and second strap members are adjustably attached to one another by means of said second attachment means to fit the helmet wearer's head near the occipital bone, said second end portions of said first and second strap members being positioned spacedly beneath said rim portion at said helmet shell rear end; wherein the combined said second end portions attached to one another by said second attachment means constitute a means for relative movement of said first and second strap members relative to one another, both pivotally about an axis transverse to said attached second end portions, and arcuately along the flexible body of said intermediate portions of said first and second strap members.

Advantageously, each said strap member further comprises several substantially ovoidal apertures which are positioned at said ribbed portion and extending generally parallel to said ribs, for conferring a greater flexibility to said strap member. Said ribs and said apertures could be positioned in an alternating fashion along said ribbed portion. Said first strap member second end portion could have in this embodiment third attachment means that are positioned on a surface opposite said second attachment means, said third attachment means for releasable attachment of said stabilizing strap to a loose flexible cord assembly integral to said helmet shell. Said first and second attachment means could be hook and loop fasteners, said second strap member overlapping said first strap member when their respective second ends are attached to one another.

This invention also concerns a head-restraining member for use on a cyclist helmet, the helmet being of the type having a shell, with internal and external walls and a peripheral edge joining the internal and external walls, and an annular rim, integral to the shell peripheral edge; said head-restraining member comprising first and second separate strap members, each strap member being elongated and comprising a main body, made from a flexible material, first attachment means, at an outer end portion of said main body, and second attachment means, at an inner end portion of said main body opposite said outer end portion thereof; wherein said first attachment means is for releasably attaching said main body to the helmet shell internal wall proximate the helmet peripheral edge, and said second attachment means of the pair of said strap members are complementary to one another for releasably interconnecting said strap members inner end portions; wherein the combined said inner end portions attached to one another by their respective complementary attachment means constitute a means for relative movement of said first and second strap members relative to one another, both pivotally about an axis transverse to said attached second end portions, and arcuately along the flexible body of said main body of said first and second strap members.

Preferably, said strap members main body further include a number of widthwise integral ribs. Each strap member could also further comprises a number of substantially ovoidal apertures, alternating between each pair of successive said ribs along said strap members main body. Each one of said first and second attachment means consists of a hook and loop band, said band of each said first attachment means adapted to cooperate with a complementary band integral to the helmet internal wall, said band of one said second attachment means forming a hook band adapted to cooperate with a loop band from the other one of said second attachment means.

DESCRIPTION OF THE DRAWINGS

FIG. 1 is a rear elevation of the stabilizing strap according to the invention;

FIG. 2 is a top edge view of the stabilizing strap with the two strap members thereof being released from one another;

FIG. 3 is a sectional view taken along line III—III of FIG. 1, at an enlarged scale;

DETAILED DESCRIPTION OF THE EMBODIMENTS

Figure 4:
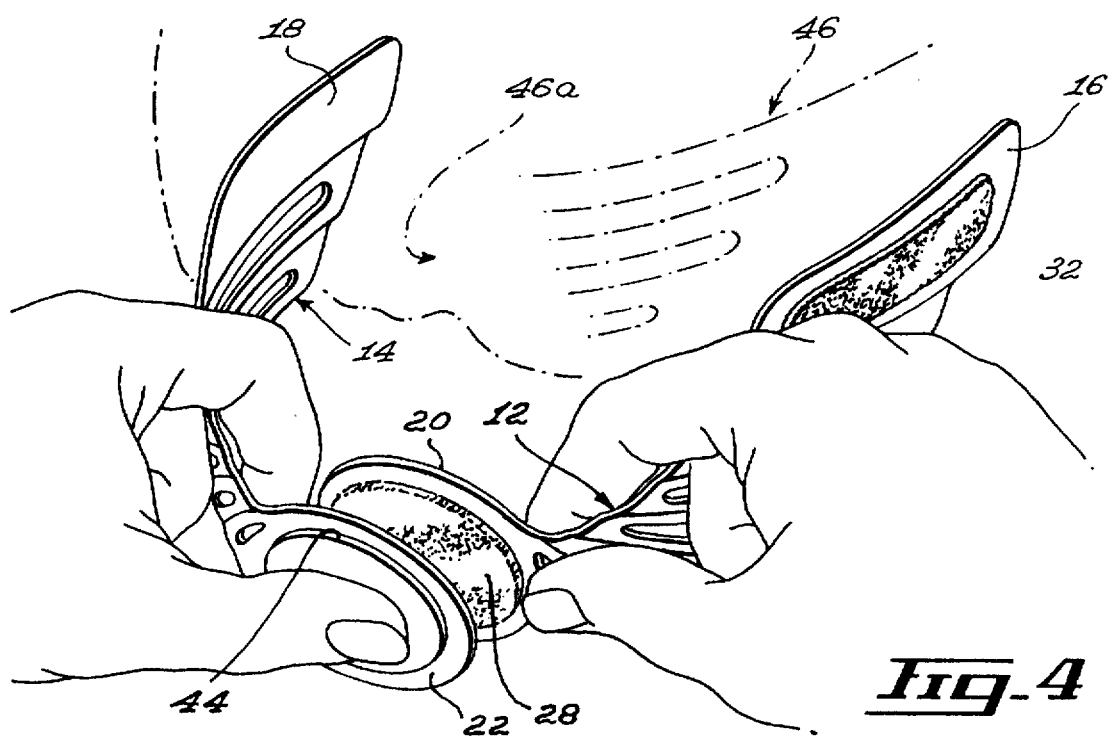
FIG. 4 is a perspective view of the stabilizing strap in operative arcuate condition, suggesting the attachment of the strap to the rear portion of a protective helmet illustrated in phantom lines.

FIGS. 1 to 4 show the preferred embodiment of the invention. The invention consists of a stabilizing strap 10 comprising a first and a second elongated curved strap members 12 and 14 made of a flexible material, preferably plastic. Each strap member 12, 14 defines respectively a first outer end portion 16, 18, a second inner end portion 20, 22 and an intermediate ribbed portion 24, 26.

Second inner end portions 20 and 22 are mirror imagbes of one another. Second strap member second end portion 22 is adapted to overlap first strap member second end portion 20, with registering complementary hook and loop fastener bands 28 and 30 that allow them to be releasably and adjustably attached to one another in this position. When attached in this manner, as shown in FIG. 1, stabilizing strap 10 is in its operative position and has an upwardly convex shape, with first end portions 16 and 18 being at the uppermost position, opposite one another.

First end portions 16 and 18 are elongated and have identical hook or loop (preferably hook) fastener bands 32, 34 on their back surface (which is the surface seen in FIG. 1).

Intermediate ribbed portions 24 and 26 each link the respective first and second ends 16 to 20, and 18 to 22, respectively. Ribbed portions 24 and 26 each defines several widthwise ribs 36, 38 which give ribbed portions 24, 26 a wavy shape (see FIG. 3), and several substantially ovoidal apertures 40, 42 positioned generally parallel to ribs 36, 38 and in an alternate fashion relative to ribs 36, 38 along ribbed portions 24, 26, respectively.

Ribs 36, 38 confer a greater transverse flexibility to strap members 12, 14. Apertures 40, 42 further have the following features:

a) they also confer a greater transverse flexibility to strap members 12, 14 while each strap member will conserve an area wide enough to comfortably distribute the pressure applied by it on the wearer's head (this matter will be detailed later); and b) allow a certain aeration to reach part of the head which stabilizing strap 10 is destined to cover.

When stabilizing band 10 is in its operative position, the flexible ribbed portions 24, 26 allow strap member first end portions 16, 18 to move relative to strap member second end portions 20, 22 in an angular fashion, because of the flexibility of ribbed portions 24, 26 (as suggested by the play in phantom lines in FIG. 1).

When stabilizing strap 10 is in its operative position and as suggested in FIG. 4, ribbed portions 24, 26 will have the greatest flexibility, first end portions 16 and 18 will have an intermediate flexibility while second end portions 20, 22 will have the least flexibility of stabilizing strap 10. The material thickness is the same all along strap 10, except for where second end portions 20 and 22 are overlapping one another, for not only does the thickness double, but also the loop and band fasteners 28 and 30 add their bulk between second end portions 20 and 22; furthermore, second end portion 22 has an increased thickness as shown at 44.

Figure 5:
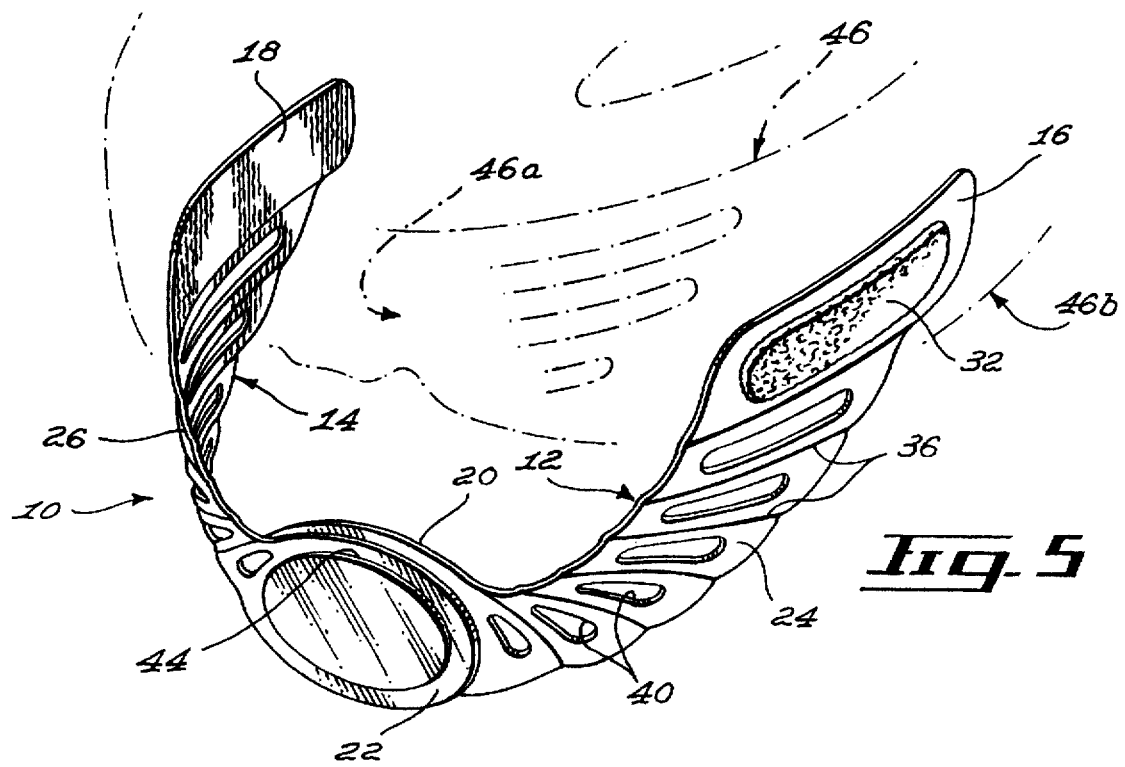
FIG. 5 is a side elevation of a cyclist head wearing a helmet, all in phantom lines, but with the helmet rear portion and associated strap member being shown in full line sectional view.
Figure 6:
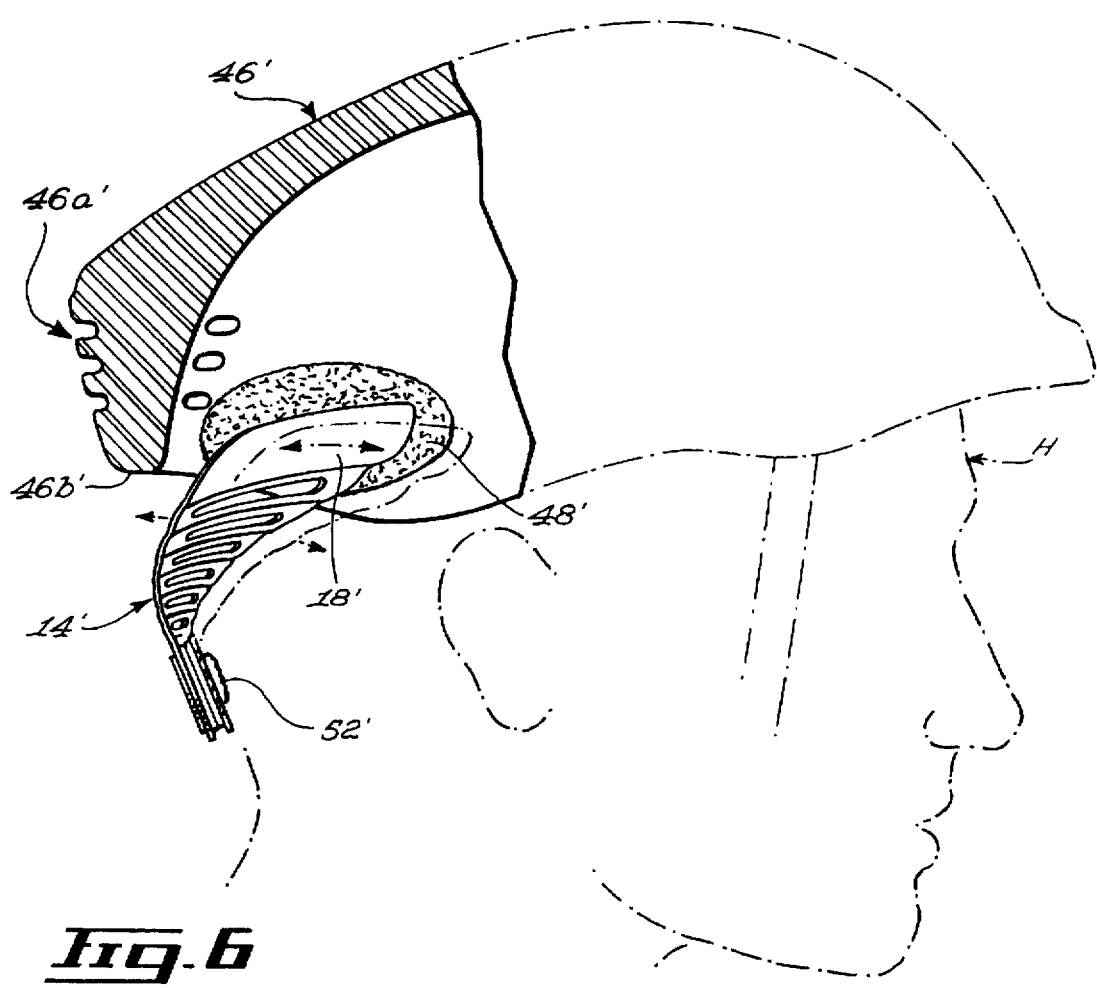
FIG. 6 is a side elevation of a cyclist head wearing a helmet, all in phantom lines, but with the helmet rear portion and associated strap member being shown in full line sectional view.

FIGS. 4 to 6 show a protective helmet 46 defining a rear end 46a (46a') and a lower peripheral rim portion 46b. Helmet 46 is destined to be placed on the wearer's head H and fastened thereto in a conventional manner. The interior part of helmet rim portion 46b has two identical hook or loop (preferably loop) fasteners 48, 48 (only one of them is shown in FIG. 5) which are complementary to fasteners 32, 34 of strap members first end portions 16, 18. Fasteners 48, 48 are positioned symmetrically and spacedly on one side and the other of the interior of rim portion 46b, near helmet rear end 46a.

In use, (FIGS. 5–6) strap members first ends 16, 18 (18') are destined to be adjustably and releasably attached to the interior surface of rim portion 46b, (46b') by means of complementary fasteners 48, or larger pad 48 (the adjustment of first end 18 is suggested in phantom lines in FIG. 6. The strap members second end portions 20, 22 are to be adjustably and releasably attached to one another by means of fasteners 28, 30, first strap member second end portion 20 being destined to bear on the occipital bone of the wearer's head H, second end portions 20, 22, thus being positioned spacedly under rim portion 46b near rear end 46a.

The relative flexibilities of first end portions 16, 18, second end portions 20, 22 and ribbed portions 24, 26 allow stabilizing strap 10 to be correctly positioned on the occipital bone of head H:

a) first end portions 16, 18, are flexible enough to curve so as to conform in shape to the curved interior surface of helmet rim portion 46b;
  b) overlapping second end portions 20, 22 are flexible enough to slightly bend but rigid enough to give a proper support to helmet 46 (46') on the head occipital bone; and
  c) ribbed portions 24, 26 are very flexible and thus bear conformingly on the head along most of their length to more evenly distribute the pressure applied by strap 10 on head H and also allow the second end portions 20, 22 to be adjustably positioned, for fitting heads of different sizes and shapes.

Consequently, if an impact blow occurs on helmet 46 that would pivot or tilt it frontwards, stabilizing strap 10 will retain helmet 10 to keep it properly positioned. Helmet 46 is thus more likely to be positioned to absorb another impact, even though it occurs on the back of the cyclist's head.

Preferably, as shown in FIGS. 3 and 6, strap member 12 (and strap member 14) (14') is covered on its interior (back) surface with a fabric coating layer 50 such as cotton, for the comfort of the wearer. Also, as shown in FIGS. 2, 5 and 6 a small pad 52 (52') is positioned on the interior surface of first strap member second end portion 20 also for the comfort of the wearer. Alternately, pad 52 can be a loop fastener, which would attach itself with a complementary hook fastener fixed on an abutment plate or a stabilizing band (both of them not shown), integral to the helmet, the purpose of which would also be to stabilize the helmet on the wearer's head.

According to the objects of the invention, another advantage of the stabilizing strap 10 is that it may be adjusted to the wearer's head size and shape while helmet 46 is worn on the cyclist's head. Indeed, the second end portions 20, 22 are spacedly positioned under rim portion 46b and can easily be reached manually. The hook and loop fasteners 28, 30 allow to easily attach or detach second inner end portions 20, 22 from one another. Therefore, the wearer of helmet 46 need not take his helmet off to adjust stabilizing strap 10.

Hence, the present invention is directed to an innovative helmet stabilizing device, which is constructed with two detachable parts molded in a thermoplastic elastomer. In effect, the present invention stabilizing device enables quick micro-fit adjustment of the helmet over the head of the wearer. The two parts of the stabilizing device are joined centrally by a hook and look fastening arrangement, such as VELCRO (registered trademark) fasteners, ergonomically enabling an improved angular adjustment of the two parts, to better fit cyclist heads of various shapes and sizes. This angular adjustment improvement can be about 30 to 40 %. The present stabilizing device is of simple design, is very practical and easy to install on or remove from the wearer's head, and can be retrofit to most existing cyclist helmet currently on the market.

I claim:

1. A flexible stabilizing strap for use on a cyclist helmet of a type having a shell with a rear end and a lower peripheral rim portion, said stabilizing strap comprising a first and a second separate elongated flexible curved strap members, each strap member comprising:

a) a first end portion having first attachment means for releasable and adjustable attachment to the helmet rim portion proximate the shell rear end;
  b) a second end portion having second attachment means for adjustable and releasable attachment to the second end portion of the other strap member, said second attachment means of said first and second strap members being complementary to one another; and
  c) an intermediate ribbed portion, having several widthwise ribs conferring a greater flexibility to said strap member; said second end portions of said first and second strap members destined to be positioned spacedly under the rim portion at the helmet rear end;

wherein the combined said second end portions attached to one another by said second attachment means constitute a means for relative movement of said first and second strap members relative to one another, both pivotally about an axis transverse to said attached second end portions, and arcuately along the flexible body of said intermediate portions of said first and second strap members.

2. A stabilizing strap as defined in claim 1, wherein each strap member further comprises several substantially ovoidal apertures which are positioned at said ribbed portion and extending generally parallel to said ribs, for conferring a greater flexibility to said strap member.

3. A stabilizing strap as defined in claim 2, wherein said ribs and said apertures are positioned in an alternating fashion along said ribbed portion.

4. A stabilizing strap as defined in claim 3, wherein said first and second attachment means are hook and loop fasteners, said second end portion of said second strap member overlapping said first strap member when attached to one another.

5. A protective helmet for cyclist comprising a stabilizing strap and defining a shell having a rear end and a lower peripheral rim portion on which is releasably and adjustably attached said stabilizing strap near said shell rear end, said stabilizing strap comprising a first and a second elongated flexible curved strap members, each strap member comprising:

a) a first end portion having first attachment means adjustably and releasably attached to the helmet rim portion;
  b) a second end portion having second attachment means adjustably and releasably attached to the second end portion of the other strap member, said second attachment means of said first and second strap members being complementary to one another; and
  c) an intermediate ribbed portion, having several widthwise ribs conferring a greater flexibility to said strap member; wherein said stabilizing strap defines an operative position when said first and second strap members are adjustably attached to one another by means of said second attachment means to fit the helmet wearer's head near the occipital bone, said second end portions of said first and second strap members being positioned spacedly beneath said rim portion at said helmet shell rear end;

wherein the combined said second end portions attached to one another by said second attachment means constitute a means for relative movement of said first and second strap members relative to one another, both pivotally about an axis transverse to said attached second end portions, and arcuately along the flexible body of said intermediate portions of said first and second strap members.

6. A protective helmet as defined in claim 5, wherein each said strap member further comprises several substantially ovoidal apertures which are positioned at said ribbed portion and extending generally parallel to said ribs, for conferring a greater flexibility to said strap member.

7. A protective helmet as defined in claim 6, wherein said ribs and said apertures are positioned in an alternating fashion along said ribbed portion.

8. A protective helmet as defined in claim 7, wherein said first and second attachment means are hook and loop fasteners, said second strap member overlapping said first strap member when their respective second ends are attached to one another.

9. A head-restraining member for use on a cyclist helmet, the helmet being of the type having a shell, with internal and external walls and a peripheral edge joining the internal and external walls, and an annular rim, integral to the shell peripheral edge; said head-restraining member comprising first and second separate strap members, each strap member being elongated and comprising a main body, made from a flexible material, first attachment means, at an outer end portion of said main body, and second attachment means, at an inner end portion of said main body opposite said outer end portion thereof;

wherein said first attachment means is for releasably attaching said main body to the helmet shell internal wall proximate the helmet peripheral edge, and said second attachment means of the pair of said strap members are complementary to one another for releasably interconnecting said strap members inner end portions;

wherein the combined said inner end portions attached to one another by their respective complementary attachment means constitute a means for relative movement of said first and second strap members relative to one another, both pivotally about an axis transverse to said attached second end portions, and arcuately along the flexible body of said main body of said first and second strap members; and wherein each strap member further comprises a number of spaced-apart, widthwise, substantially ovoidal and parallel apertures thereon.

10. A head-restraining member as defined in claim 9, wherein each said strap member main body further includes a number of widthwise integral ribs, located in an alternate fashion between each pair of successive said ovoidal apertures along said strap member main body.

11. A head-restraining member as defined in claim 9, wherein each one of said first and second attachment means consists of a hook and loop band, said band of each said first attachment means adapted to cooperate with a complementary band integral to the helmet internal wall, said band of one said second attachment means forming a hook band adapted to cooperate with a loop band from the other one of said second attachment means.

\* \* \* \* \*